United States Patent
Sheng et al.

(10) Patent No.: US 10,660,963 B2
(45) Date of Patent: May 26, 2020

(54) PHARMACEUTICAL COMPOSITION CONTAINING TACROLIMUS AND PREPARATION METHODS THEREOF

(71) Applicant: Hangzhou SoliPharma Co., Ltd., Hangzhou, Zhejiang (CN)

(72) Inventors: Xiaoxia Sheng, Zhejiang (CN); Yong Tang, Zhejiang (CN)

(73) Assignee: Hangzhou SoliPharma Co., Ltd., Hangzhou, Zhejang (CN)

( * ) Notice: Subject to any disclaimer, the term of this patent is extended or adjusted under 35 U.S.C. 154(b) by 0 days.

(21) Appl. No.: 15/998,503

(22) Filed: Aug. 16, 2018

(65) Prior Publication Data

US 2019/0083627 A1    Mar. 21, 2019

Related U.S. Application Data

(62) Division of application No. 15/122,675, filed as application No. PCT/CN2015/091438 on Oct. 8, 2015, now abandoned.

(30) Foreign Application Priority Data

Nov. 21, 2014   (CN) .......................... 2014 1 0675082

(51) Int. Cl.
| | | |
|---|---|---|
| *A61K 31/436* | (2006.01) | |
| *A61K 47/12* | (2006.01) | |
| *A61K 47/26* | (2006.01) | |
| *A61K 47/38* | (2006.01) | |
| *A61K 9/48* | (2006.01) | |
| *A61K 9/16* | (2006.01) | |

(52) U.S. Cl.
CPC ............ *A61K 47/38* (2013.01); *A61K 9/1652* (2013.01); *A61K 9/48* (2013.01); *A61K 31/436* (2013.01); *A61K 47/12* (2013.01); *A61K 47/26* (2013.01)

(58) Field of Classification Search
CPC ...... A61K 31/436; A61K 47/12; A61K 47/26; A61K 47/38; A61K 9/48
See application file for complete search history.

(56) References Cited

U.S. PATENT DOCUMENTS

| | | |
|---|---|---|
| 6,440,458 B1 | 8/2002 | Yamashita et al. |
| 2002/0044967 A1 | 4/2002 | Yamashita et al. |
| 2002/0099067 A1 | 7/2002 | Posanski |
| 2006/0287352 A1 | 12/2006 | Holm et al. |
| 2007/0270451 A1 | 11/2007 | Gyollai et al. |
| 2013/0216624 A1 | 8/2013 | Lee |
| 2017/0072058 A1 | 3/2017 | Sheng et al. |

FOREIGN PATENT DOCUMENTS

| | | |
|---|---|---|
| CN | 1820759 A | 8/2006 |
| CN | 101098875 A | 1/2008 |
| EP | 0240773 B1 | 10/1987 |
| EP | 1421939 A1 | 5/2014 |
| KR | 10-0092145 | 7/1995 |
| KR | 10-0440553 B1 | 6/2004 |
| WO | WO 95/01785 A1 | 1/1995 |
| WO | WO 99/49863 | 10/1999 |
| WO | WO 2012/053785 A2 | 4/2012 |
| WO | WO 2016/078481 A1 | 5/2016 |

OTHER PUBLICATIONS

International Search Report for International Application No. PCT/CN2015/091438, ISA, China, dated Jan. 8, 2015, 4 pages.
Written Opinion for International Application No. PCT/CN2015/091438, ISA, China, dated Jan. 8, 2016, 8 pages.
Non-Final Office action dated Oct. 11, 2017, in U.S. Appl. No. 15/122,675, inventor Sheng, X., et al., filed Aug. 31, 2016, 7 pages.
Final Office action dated May 16, 2018, in U.S. Appl. No. 15/122,675, inventor Sheng, X., et al., filed Aug. 31, 2016, 8 pages.

*Primary Examiner* — Zohreh A Fay
(74) *Attorney, Agent, or Firm* — Sterne Kessler Goldstein & Fox PLLC

(57) ABSTRACT

Disclosed are a pharmaceutical composition comprising tacrolimus and a preparation method thereof.

14 Claims, No Drawings

PHARMACEUTICAL COMPOSITION CONTAINING TACROLIMUS AND PREPARATION METHODS THEREOF

FIELD OF THE INVENTION

The invention relates to the field of pharmaceuticals technology. Specifically, the present invention relates to a pharmaceutical composition containing tacrolimus and methods for preparing the composition.

BACKGROUND

Tacrolimus, also named FK506, is a macrolide pharmaceutical compound with the molecular formula $C_{44}H_{69}NO_{12} \cdot H_2O$ and molecular weight 882.05, having the chemical structural formula shown below:

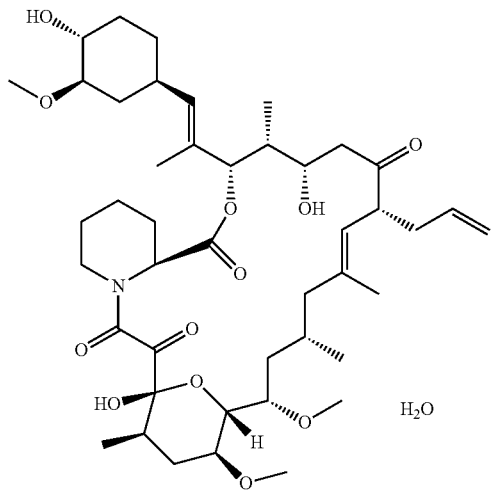 [SMILES: C=CC[C@@H]1/C=C(\C)C[C@H](C)C[C@H](OC)[C@H]2O[C@@](O)(C(=O)C(=O)N3CCCC[C@H]3C(=O)O[C@H](/C(C)=C/[C@@H]3CC[C@@H](O)[C@H](OC)C3)[C@H](C)[C@@H](O)CC1=O)[C@H](C)C[C@@H]2OC ; O]

Tacrolimus has expanded indications. It was initially used as graft rejection inhibitor for organ transplant patients. Later it was developed as ointment formulations for treating atopic dermatitis, and was further used as therapeutic agents for other inflammatory skin diseases. Currently, the dosage forms of tacrolimus are capsules, extended release capsules, ointment and so on.

The solubility of tacrolimus in water is extremely low and is only 1 to 2 μg/ml. When orally administered, tacrolimus in formulations can't be rapidly released, which leads to insufficient absorption rate in the body and thus causes lower drug bioavailability. In addition, there are significant variations between individuals after oral administration.

To solve these problems, various inventors have proposed different solutions, for example, Korean patent 10-0092145 disclosed dissolving tacrolimus in organic solvents, using hydroxypropyl methylcellulose as a dispersing carrier and preparing the mixture into a solid dispersion to improve its release rate; patent document WO95/01785 related to using nonionic surfactant polyglycerol fatty oils and sortitan anhydride fatty acid esters to improve its solubility; patent documents WO99/49863, EP1421939A1 and Korean patent 10-0440553 disclosed preparing sustained-release formulations (commercially available product) comprising: dissolving both the ethyl cellulose and tacrolimus in organic solvents, and then granulating the mixture with hydroxypropyl methylcellulose and lactose, drying the granules and milling the granules; patent document WO2012/053785A2 disclosed sustained-release pellets containing tacrolimus as the active ingredient. According to the patent specification, the sustained-release pellets consist of a five-layer structure including a core, a pharmacological active ingredient layer, a primary pharmacological inactive ingredient layer, a sustained-release layer, a secondary pharmacological inactive ingredient layer and an initial release membrane layer containing tacrolimus; patent document EP0240773B1 described a preparation method of immediate release capsules containing tacrolimus, which comprises dissolving tacrolimus in ethanol, adding hydroxypropyl methylcellulose as dispersing agent and dissolving the mixture in dichloromethane, preparing soft materials and drying, milling, sieving and filling; patent document CN1820759A described a preparation method of tacrolimus solid dispersion, wherein the active substance and carrier materials at mass ratios of 1:5-1:20 were prepared by the solvent method, the solvent-melting method or the freeze and drying method; patent document CN101098875A disclosed an amorphous tacrolimus and formulations containing amorphous tacrolimus comprising diluents, adhesives, disintegrants, glidants, lubricants, flavor correcting agent/flavor enhancing agent or colorants according to different usage.

The present inventors found that the formulations and preparation processes reported in EP0240773B1 and CN1820759A used dichloromethane. Dichloromethane is a Class II organic solvent and should be limited to use. The tacrolimus products prepared by the methods disclosed in other documents as discussed above have the problems of crystallization of tacrolimus in the dissolution medium or in vivo causing incomplete dissolution of tacrolimus and low drug plasma concentration and low drug efficacy.

To solve of the above problems, the present inventors eliminated organic solvent dichloromethane in preparation processes, which reduces the hazards to operators and environment and shortens operation procedures. Meanwhile, crystallization of tacrolimus in dissolution medium or in vivo can be avoided by regulating the amount of crystallization inhibitor used in the formulation, and thus avoiding low drug plasma concentration and low drug efficacy caused by the incomplete dissolution of tacrolimus. Also, the crystallization inhibitor can reduce the transformation of amorphous tacrolimus to crystalline form of tacrolimus in storage and can improve the stability of the drug.

SUMMARY OF THE INVENTION

The object of the present invention is to provide a pharmaceutical composition comprising tacrolimus, specifically an oral formulation containing tacrolimus.

A pharmaceutical composition containing tacrolimus, which comprises an active pharmaceutical ingredient, tacrolimus, and other pharmaceutically acceptable fillers, adhesives, disintegrants, lubricants, wherein the pharmaceutical composition also contains a crystallization inhibitor and the mass ratio of tacrolimus and the crystallization inhibitor is 1:0.5 to 1:2.5.

Preferably, the crystallization inhibitor is polyvinyl pyrrolidone or hydroxypropyl methylcellulose, more preferably hydroxypropyl methylcellulose.

Preferably, the filler is selected from the group consisting of sucrose, mannitol, lactose, starch, and microcrystalline cellulose, more preferably lactose.

Preferably, the disintegrant is selected from the group consisting of cross-linked polyvinyl polypyrrolidone, sodium carboxymethyl starch, cross-linked sodium carboxymethylcellulose, and low substituted hydroxypropyl cellulose, more preferably cross-linked sodium carboxymethylcellulose.

Preferably, lubricant is selected from the group consisting of stearic acid, magnesium stearate, polyethylene glycol 6000, and castor oil hydrogenated, more preferably magnesium stearate.

A preparation method of the pharmaceutical composition containing tacrolimus comprises the following procedures:

(1) preparing solution: dissolving the tacrolimus in ethanol and obtaining a clear solution;

(2) preparing premixed excipients: mixing hydroxypropyl methylcellulose, cross-linked sodium carboxymethylcellulose and lactose homogeneously using a wet granulation machine and obtaining premixed excipients;

(3) preparing soft materials: mixing the solution obtained in procedure (1) and premixed excipients obtained in procedure (2) by a wet granulation machine and obtaining soft materials by wet granulation;

(4) drying the soft materials in a vacuum oven at 50° C. and granulating by forcing the materials through a 40-mesh sieve using a granulating machine;

(5) adding lactose and magnesium stearate into the above granulated mass, mixing homogeneously, and filling the granules into hard capsule shells.

The advantages of the dosage form prepared according to the above composition are as follows:

1. Compared to preparation processes of tacrolimus formulations in the prior art, the present invention eliminates using dichloromethane, which reduces the hazards to operators and environment and shortens operation procedures.

2. Dissolution experiments in vitro indicates that dissolution of tacrolimus solid dispersion containing crystallization inhibitor hydroxypropyl methylcellulose is greater than that of amorphous tacrolimus, illustrating that adding crystallization inhibitor hydroxypropyl methylcellulose inhibits tacrolimus crystallization in the dissolution medium and is helpful to increase the dissolution rate of tacrolimus and the amount of tacrolimus dissolved.

3. Dissolution experiments in vitro demonstrates that crystallization inhibitor hydroxypropyl methylcellulose used in the present invention can inhibit tacrolimus phase transition in the dissolution medium and can avoid tacrolimus crystallization in the dissolution medium or in vivo and thus avoid low drug plasma concentration and low drug efficacy caused by the incomplete dissolution of tacrolimus.

EXAMPLES

The following examples are given for further understanding the present invention but are not used for limiting the scope of the present invention. Unless particularly specified, the percentage is weight percentage.

Instruments and methods used for data collection are as follows:

High performance liquid chromatography (HPLC) data were collected using Agilent 1100 under the following conditions: $C_8$ column (250 mm×4.6 mm), column temperature 50° C., detector wavelength 210 nm, flow rate 0.75 mL/min, injection volume 800 μL, elution time about 23 min. Mobile phase is a mixture of acetonitrile:methanol:water:diluted phosphoric acid (3.0 ml phosphoric acid in 50.0 ml water)=460:360:180:1, equal degree elution.

Unless particularly specified, the examples in the present invention were conducted at room temperature.

Tacrolimus used in the examples was commercially purchased and was crystalline tacrolimus.

Unless particularly specified, all reagents used in the examples were commercially purchased.

Preparation Example 1

The capsule formulations containing tacrolimus were prepared by reference to the preparation process in example 11 of the patent document CN1820759A. The process is specified as follows:

Place 1 g of tacrolimus and 5 g of hydroxypropyl methylcellulose (E3) in a beaker, add 25 ml of anhydrous ethanol and 25 ml of dichloromethane, stir to dissolve completely, rotary evaporate the solvents for 25 minutes in a 50° C. water bath until dryness, freeze and dry the mixture for 24 h, take the solids out of the drier, grind, pass the solids through a 80-mesh sieve and obtain tacrolimus solid dispersion.

Encapsulate the tacrolimus solid dispersion with the strength of 1 mg of tacrolimus.

Example 1

A formula of tacrolimus capsules is shown in the following table:

| Name | Per capsule(mg) | Percentage of component(%) |
| --- | --- | --- |
| Tacrolimus | 1 | 1.7 |
| Lactose | 1.6 | 2.7 |
| Hydroxypropyl methylcellulose | 1 | 1.7 |
| Cross-linked sodium carboxymethylcellulose | 0.4 | 0.7 |
| Lactose (Additional) | 55 | 91.7 |
| Magnesium stearate (Additional) | 1 | 1.7 |
| Ethanol | 2.5 | N/A |
| Total | 60 | 100.0 |

Preparation procedures are as follows:

(1) preparing solution: weighing 24 g of tacrolimus and dissolving the tacrolimus in 60 g of ethanol;

(2) preparing premixed excipients: mixing 24 g of hydroxypropyl methylcellulose, 4.8 g of cross-linked sodium carboxymethylcellulose and 38.4 g of lactose homogeneously using a wet granulating machine;

(3) preparing soft materials: mixing the solution obtained in procedure (1) and premixed excipients obtained in procedure (2) using a wet granulating machine and obtaining soft materials;

(4) drying the soft materials in a vacuum oven at 50° C.;

(5) granulating by forcing the soft materials obtained in procedure (4) through a 40-mesh sieve; adding 1320 g of lactose and 24 g of magnesium stearate into the granulated mass, mixing homogeneously, and filling the granules into hard capsule shells.

Example 2

A formula of tacrolimus capsules is shown in the following table:

| Name | Per capsule(mg) | Percentage of component(%) |
|---|---|---|
| Tacrolimus | 1 | 1.7 |
| Lactose | 0.6 | 1.0 |
| Hydroxypropyl methylcellulose | 2.5 | 4.2 |
| Cross-linked sodium Carboxymethylcellulose | 0.4 | 0.7 |
| Lactose (additional) | 54.5 | 90.8 |
| Magnesium stearate (additional) | 1 | 1.7 |
| Ethanol | 2.5 | N/A |
| Total | 60 | 100.0 |

Preparation procedures of the capsules are the same as those of Example 1.

Example 3

A formula of tacrolimus capsules is shown in the following table:

| Name | Per capsule (mg) | Percentage of component(%) |
|---|---|---|
| Tacrolimus | 1 | 1.7 |
| Lactose | 2.6 | 4.3 |
| Hydroxypropyl methylcellulose | 2 | 3.3 |
| Cross-linked sodium Carboxymethylcellulose | 0.4 | 0.7 |
| Lactose (additional) | 53 | 88.3 |
| Magnesium stearate (additional) | 1 | 1.7 |
| Ethanol | 2.5 | N/A |
| Total | 60 | 100.0 |

Preparation procedures of the capsules are the same as those of Example 1.

Example 4

A formula of tacrolimus capsules is shown in the following table:

| Name | Per capsule(mg) | Percentage of component(%) |
|---|---|---|
| Tacrolimus | 1 | 1.7 |
| Lactose | 1.7 | 2.8 |
| Hydroxypropyl methylcellulose | 0.5 | 0.8 |
| Cross-linked sodium Carboxymethylcellulose | 0.4 | 0.7 |
| Lactose (additional) | 55.4 | 92.3 |
| Magnesium stearate (additional) | 1 | 1.7 |
| Ethanol | 2.5 | N/A |
| Total | 60 | 100.0 |

Preparation procedures of the capsules are the same as those of Example 1.

Example 5

A formula of tacrolimus capsules is shown in the following table:

| Name | Per capsule(mg) | Percentage of component(%) |
|---|---|---|
| Tacrolimus | 1 | 1.7 |
| Mannitol | 1.6 | 2.7 |
| Hydroxypropyl methylcellulose | 1 | 1.7 |
| Cross-linked sodium carboxymethylcellulose | 0.4 | 0.7 |
| Microcrystalline cellulose (additional) | 55 | 91.7 |
| Magnesium stearate (additional) | 1 | 1.7 |
| Ethanol | 2.5 | N/A |
| Total | 60 | 100.0 |

Preparation procedures are as follows:

(1) preparing solution: weighing 24 g of tacrolimus and dissolving the tacrolimus in 60 g of ethanol, (2) preparing premixed excipients: mixing 24 g of hydroxypropyl methylcellulose, 4.8 g of cross-linked sodium carboxymethylcellulose and 38.4 g of mannitol homogeneously using a wet granulating machine, (3) preparing soft materials: mixing the solution obtained in procedure (1) and premixed excipients obtained in procedure (2) using a wet granulating machine and obtaining soft materials, (4) drying the soft materials in a vacuum oven at 50° C., (5) granulating by forcing the soft materials obtained in procedure (4) through a 40-mesh sieve; adding 1320 g of lactose and 24 g of magnesium stearate into the granulated mass, mixing homogeneously, and filling the granules into hard capsule shells.

Example 6

A formula of tacrolimus capsules is shown in the following table:

| Name | Per capsule(mg) | Percentage of component(%) |
|---|---|---|
| Tacrolimus | 1 | 1.7 |
| Lactose | 1.6 | 2.7 |
| Polyvinyl polypyrrolidone | 1 | 1.7 |
| Sodium carboxymethyl starch | 0.4 | 0.7 |
| Lactose (additional) | 55 | 91.7 |
| Stearic acid (additional) | 1 | 1.7 |
| Ethanol | 2.5 | N/A |
| Total | 60 | 100.0 |

Preparation procedures are as follows:

(1) preparing solution: weighing 24 g of tacrolimus and dissolving the tacrolimus in 60 g of ethanol, (2) preparing premixed excipients: mixing 24 g of polyvinyl polypyrrolidone, 4.8 g of sodium carboxymethyl and 38.4 g of lactose homogeneously using a wet granulating machine, (3) preparing soft materials: mixing the solution obtained in procedure (1) and premixed excipients obtained in procedure (2) using a wet granulating machine and obtaining soft materials, (4) drying the soft materials in a vacuum oven at 50° C., (5) granulating by forcing the soft materials obtained in procedure (4) through a 40-mesh sieve; adding 1320 g of lactose and 24 g of stearic acid into the granulated mass, mixing homogeneously, and filling the granules into hard capsule shells.

Example 7

A formula of tacrolimus capsules is shown in the following table:

| Name | Per capsule(mg) | Percentage of component(%) |
|---|---|---|
| Tacrolimus | 1 | 1.7 |
| Lactose | 1.6 | 2.7 |
| Polyvinyl pyrrolidone | 1 | 1.7 |
| Sodium carboxymethyl starch | 0.4 | 0.7 |
| Lactose (additional) | 55 | 91.7 |
| Stearic acid (additional) | 1 | 1.7 |
| Ethanol | 2.5 | N/A |
| Total | 60 | 100.0 |

Preparation procedures are as follows:

(1) preparing solution: weighing 24 g of tacrolimus and dissolving the tacrolimus in 60 g of ethanol, (2) preparing premixed excipients: mixing 24 g of polyvinyl pyrrolidone, 4.8 g of sodium carboxymethyl and 38.4 g of lactose homogeneously using a wet granulating machine, (3) preparing soft materials: mixing the solution obtained in procedure (1) and premixed excipients obtained in procedure (2) using a wet granulating machine and obtaining soft materials, (4) drying the soft materials in a vacuum oven at 50° C., (5) granulating by forcing the soft materials obtained in procedure (4) through a 40-mesh sieve; adding 1320 g of lactose and 24 g of stearic acid into the granulated mass, mixing homogeneously, and filling the granules into hard capsule shells.

Example 8

A formula of tacrolimus capsules is shown in the following table:

| Name | Per capsule(mg) | Percentage of component(%) |
|---|---|---|
| Tacrolimus | 1 | 1.7 |
| Lactose | 1.6 | 2.7 |
| Hydroxypropyl methylcellulose | 1 | 1.7 |
| Cross-linked polyvinyl pyrrolidone | 0.4 | 0.7 |
| Starch (additional) | 55 | 91.7 |
| Talc (additional) | 1 | 1.7 |
| Ethanol | 2.5 | N/A |
| Total | 60 | 100.0 |

Preparation procedures are as follows:

(1) preparing solution: weighting 24 g of tacrolimus and dissolving the tacrolimus in 60 g of ethanol, (2) preparing premixed excipients: mixing 24 g of hydroxypropyl methylcellulose, 4.8 g of cross-linked polyvinyl pyrrolidone and 38.4 g of lactose homogeneously using a wet granulating machine, (3) preparing soft materials: mixing the solution obtained in procedure (1) and premixed excipients obtained in procedure (2) using a wet granulating machine and obtaining soft materials, (4) drying in a vacuum oven at 50° C., (5) granulating by forcing the above soft materials through a 40-mesh sieve; adding 1320 g of starch and 24 g of talc into the granulated mass, mixing homogeneously, and filling the granules into hard capsule shells.

Preparation Example 2

A formula of tacrolimus capsule is shown in the following table:

| Name | Per capsule(mg) | Percentage of component(%) |
|---|---|---|
| Tacrolimus | 1 | 1.7 |
| Lactose | 1.6 | 2.7 |
| Cross-linked sodium carboxymethylcellulose | 0.4 | 0.7 |
| Lactose (additional) | 55 | 91.7 |
| Magnesium stearate (additional) | 1 | 1.7 |
| Ethanol | 2.5 | N/A |
| Total | 60 | 100.0 |

Preparation procedures are as follows:

(1) preparing solution: weighting 24 g of tacrolimus and dissolving the tacrolimus in 60 g of ethanol, (2) preparing premixed excipients: mixing 4.8 g of cross-linked sodium carboxymethylcellulose and 38.4 g of lactose homogeneously using a wet granulating machine, (3) preparing soft materials: mixing the solution obtained in procedure (1) and premixed excipients obtained in procedure (2) using a wet granulating machine and obtaining soft materials, (4) drying in a vacuum oven at 50° C., (5) granulating by forcing the above soft materials through a 40-mesh sieve; adding 1320 g of starch and 24 g of talc into the granulated mass, mixing homogeneously, and filling the granules into hard capsule shells.

Comparative Example 1

Dissolve tacrolimus in anhydrous ethanol, prepare amorphous tacrolimus by rotary evaporation to remove the solvent, prepare solid dispersion with the amorphous tacrolimus and hydroxypropyl methylcellulose at the ratio of 5:1 (g/g). Prepare the capsules of amorphous tacrolimus and capsules of solid dispersion according to the present invention, and compare their dissolution in vitro. The dissolution methods are based on the methods in FDA dissolution database, using the paddle method with a rotational speed of 50 rpm and a dissolution medium of 900 mL pH 4.5 water solution (adjusted by 1% phosphoric acid) containing 0.005% hydroxypropyl cellulose. Sample 10 ml of solutions at the time of 30 minutes, 60 minutes, 90 minutes and 120 minutes respectively, filter through 0.45 μm membrane, take 5.0 ml filtrate, add 2.0 ml of acetonitrile, shake, test the solution by HPLC and calculate percent tacrolimus dissolved. After each sampling, add 10 ml of blank dissolution medium back to the dissolution apparatus. The dissolution data of amorphous tacrolimus and solid dispersion are shown in the following table:

Comparison of Percent of Tacrolimus Dissolved
Between Amorphous Tacrolimus Capsules and
Solid Dispersion Capsules

| Time (min) | Amorphous tacrolimus capsules (%) | Solid dispersion capsules (%) |
|---|---|---|
| 30 | 18.6 | 28.6 |
| 60 | 33.6 | 45.4 |
| 90 | 65.3 | 78.1 |
| 120 | 53.1 | 89.4 |

According to the in vitro dissolution results, the percent (of tacrolimus) dissolved from the solid dispersion capsules according to the present invention is significantly higher than that of amorphous tacrolimu capsules. At the time of 120 minutes, the percent of tacrolimus dissolved from amorphous tacrolimus capsules decreased as some amorphous tacrolimus crystallized and precipitated out, while the percent of tacrolimus dissolved from solid dispersion containing hydroxypropyl methylcellulose increases continuously, indicating that adding hydroxypropyl methylcelluloseas crystallization inhibitor can inhibit tacrolimus crystallization in the dissolution medium and is helpful to increase the dissolution rate and amount of tacrolimus dissolved.

Comparative Example 2

Compare the dissolution in vitro between tacrolimus capsules prepared in the present invention (Example 1 and Example 4) and the capsules prepared in preparation Example 2. The dissolution methods are based on the method in FDA dissolution database, using the paddle method with a rotational speed of 50 rpm, and a dissolution medium of 900 mL pH 4.5 water solution (adjusted by using 1% phosphoric acid) containing 0.005% hydroxypropyl cellulose. Sample 10 ml of solutions at the time of 30 minutes, 60 minutes, 90 minutes and 120 minutes respectively, filter through 0.45 μm membrane, take 5.0 ml filtrate, add 2.0 ml of acetonitrile, shake, test the solution by HPLC and calculate the percent tacrolimus dissolved. After each sampling, add 10 ml of blank dissolution medium back to the dissolution apparatus. The dissolution data of capsules prepared in the present invention and capsules prepared in Preparation Example 2 are shown in the following table:

Comparison of Percent of Tacrolimus Dissolved
Between Capsules Prepared in Example 1, Example
4 and Preparation Example 2

| Time (min) | Capsules of Example 1 average % | Capsules of Example 4 average % | Capsules of Preparation Example 2 average % |
|---|---|---|---|
| 30 | 31.6 | 27.9 | 26.7 |
| 60 | 51.6 | 45.8 | 40.1 |
| 90 | 68.3 | 55.1 | 20.8 |
| 120 | 72.7 | 50.7 | 10.6 |

The mass percentage of crystallization inhibitor hydroxypropyl methylcellulose in capsules prepared in Example 1, Example 4 and Preparation Example 2 is 1.7%, 0.8% and 0.0%, respectively. According to the above dissolution experiment result, at the end of dissolution test the percent of tacrolimus dissolved increases with the increasing amount of crystallization inhibitor hydroxypropyl methylcellulose. The result indicates that crystallization inhibitor hydroxypropyl methylcellulose used in the present invention can inhibit tacrolimus phase transformation in the dissolution medium and can avoid tacrolimus crystallization in the dissolution medium or in vivo and thus avoid low plasma concentration and low drug efficacy caused by the incomplete dissolution of tacrolimus.

Above mentioned are only embodiments of the present invention, which do not cover the entire protection scope of the present invention. Within the technical scope revealed in the present invention, modifications or replacements made by those skilled in the art without creative labor should all be within the protection scope of the present invention.

What is claimed is:

1. A method of preparing a pharmaceutical composition comprising tacrolimus, the method comprising:
   (1) preparing a solution: dissolving tacrolimus in ethanol and obtaining a clear solution,
   (2) preparing premixed excipients: mixing a crystallization inhibitor, a disintegrant and a pharmaceutically acceptable filler homogeneously using a wet granulating machine and obtaining premixed excipients,
   (3) preparing soft materials: mixing the solution obtained in procedure (1) and the premixed excipients obtained in procedure (2) using a wet granulating machine and obtaining soft materials by wet granulation,
   (4) drying the soft materials in a vacuum oven at 50° C. and granulating by forcing the soft materials through a 40-mesh sieve using a granulating machine, and
   (5) adding a pharmaceutically acceptable filler and a lubricant into the granulated mass, mixing homogeneously, and filling in hard capsule shells,
   wherein the mass ratio of tacrolimus to the crystallization inhibitor is 1:0.5 to 1:2.5.

2. The method according to claim 1, wherein the crystallization inhibitor is polyvinyl pyrrolidone or hydroxylpropyl methylcellulose.

3. The method according to claim 2, wherein the crystallization inhibitor is hydroxypropyl methylcellulose.

4. The method according to claim 1, wherein the pharmaceutically acceptable filler is selected from the group consisting of sucrose, mannitol, lactose, starch and microcrystalline cellulose.

5. The method according to claim 4, wherein the pharmaceutically acceptable filler is lactose.

6. The method according to claim 1, wherein the disintegrant is selected from the group consisting of cross-linked polyvinyl pyrrolidone, sodium carboxymethyl starch, cross-linked sodium carboxymethylcellulose and low substituted hydroxypropyl cellulose.

7. The method according to claim 6, wherein the disintegrant is cross-linked sodium carboxymethylcellulose.

8. The method according to claim 1, wherein the lubricant is selected from the group consisting of stearic acid, magnesium stearate, polyethylene glycol 6000 and castor oil hydrogenated.

9. The method according to claim 8, wherein the lubricant is magnesium stearate.

10. The method according to claim 1, wherein the crystallization inhibitor is polyvinyl pyrrolidone or hydroxypropyl methylcellulose; the pharmaceutically acceptable filler is selected from the group consisting of sucrose, mannitol, lactose, starch and microcrystalline cellulose; the disintegrant is selected from the group consisting of cross-linked polyvinyl pyrrolidone, sodium carboxymethyl starch, cross-linked sodium carboxymethylcellulose and low substituted hydroxypropyl cellulose; and the lubricant is selected from the group consisting of stearic acid, magnesium stearate, polyethylene glycol 6000 and castor oil hydrogenated.

11. The method according to claim 1, wherein the crystallization inhibitor is hydroxypropyl methylcellulose; the pharmaceutically acceptable filler is lactose; the disintegrant is cross-linked sodium carboxymethylcellulose; and the lubricant is magnesium stearate.

12. The method according to claim 1, wherein the pharmaceutical composition further comprises an adhesive.

13. A method of preparing a pharmaceutical composition comprising tacrolimus, comprising:
- (1) preparing a solution: dissolving tacrolimus in ethanol and obtaining a clear solution,
- (2) preparing premixed excipients: mixing hydroxypropyl methylcellulose, cross-linked sodium carboxymethylcellulose and lactose homogeneously using a wet granulating machine and obtaining premixed excipients,
- (3) preparing soft materials: mixing the solution obtained in procedure (1) and the premixed excipients obtained in procedure (2) using a wet granulating machine and obtaining soft materials by wet granulation,
- (4) drying the soft materials in a vacuum oven at 50° C. and granulating by forcing the soft materials through a 40-mesh sieve using a granulating machine, and
- (5) adding lactose and magnesium stearate into the granulated mass, mixing homogeneously, and filling in hard capsule shells.

14. The method according to claim 13, wherein the pharmaceutical composition further comprises an adhesive.

* * * * *